(12) United States Patent
Hallinder et al.

(10) Patent No.: US 6,474,347 B1
(45) Date of Patent: Nov. 5, 2002

(54) DENTAL FLOSS HOLDER

(76) Inventors: Anders Hallinder, Valhallavagen 16, S-191 49 Sollentuna (SE); Pekka Sihvo, Radmansgatan 25, 114 25 Stockholm (SE)

( * ) Notice: Subject to any disclaimer, the term of this patent is extended or adjusted under 35 U.S.C. 154(b) by 0 days.

(21) Appl. No.: 09/890,046

(22) PCT Filed: Jan. 27, 2000

(86) PCT No.: PCT/US00/02201

§ 371 (c)(1),
(2), (4) Date: Jul. 25, 2001

(87) PCT Pub. No.: WO00/44301

PCT Pub. Date: Aug. 3, 2000

(30) Foreign Application Priority Data

Jan. 28, 1999 (SE) .............................. 9900275

(51) Int. Cl.⁷ .............................. A61C 15/00
(52) U.S. Cl. .................. 132/325; 132/323; 132/324
(58) Field of Search ................... 132/325, 323, 132/324, 326, 327, 328, 329

(56) References Cited

U.S. PATENT DOCUMENTS

| | | | |
|---|---|---|---|
| 2,577,597 A | * 12/1951 | Wright et al. | 132/325 |
| 3,814,114 A | * 6/1974 | Roberts | 132/323 |
| 3,924,647 A | 12/1975 | Lindblad | |
| 4,518,000 A | * 5/1985 | Leverette | 132/323 |
| 4,790,336 A | 12/1988 | Kuo | 132/325 |
| 5,020,554 A | * 6/1991 | Feinberg | 132/323 |
| 5,038,806 A | 8/1991 | Ewald | 132/325 |
| 5,085,236 A | 2/1992 | Odneal et al. | 132/325 |
| 5,253,662 A | 10/1993 | Won | 132/325 |
| 5,375,614 A | 12/1994 | Navratil | 132/325 |
| 5,375,615 A | 12/1994 | Wahlstrom | 132/325 |
| 5,573,022 A | 11/1996 | Winters | 132/325 |
| 5,678,578 A | 10/1997 | Kossak et al. | 132/322 |

* cited by examiner

*Primary Examiner*—John J. Wilson
*Assistant Examiner*—Robyn Kieu Doan
(74) *Attorney, Agent, or Firm*—Fasth Law Offices; Rolf Fasth

(57) ABSTRACT

A dental floss holder that has an elongate handle member (1) that has two fork fingers (2) at one end and wherein a floss supply (5) is mounted to the member (1) for pulling out of the dental floss (64–68) therefrom, and wherein points (3) of the fingers (2) have guidance members for the floss to permit a floss segment (66) to extend between the finger points (3) and wherein the members (91–97) are provided to attach a floss end (68) to the member (1). The dental floss supply (5) includes a floss roll (60) which is mounted with its rolling axle perpendicular to the elongate handle member (1). The locking members (56, 80, 84) are provided to lock the roll (60) from rotation,

4 Claims, 1 Drawing Sheet

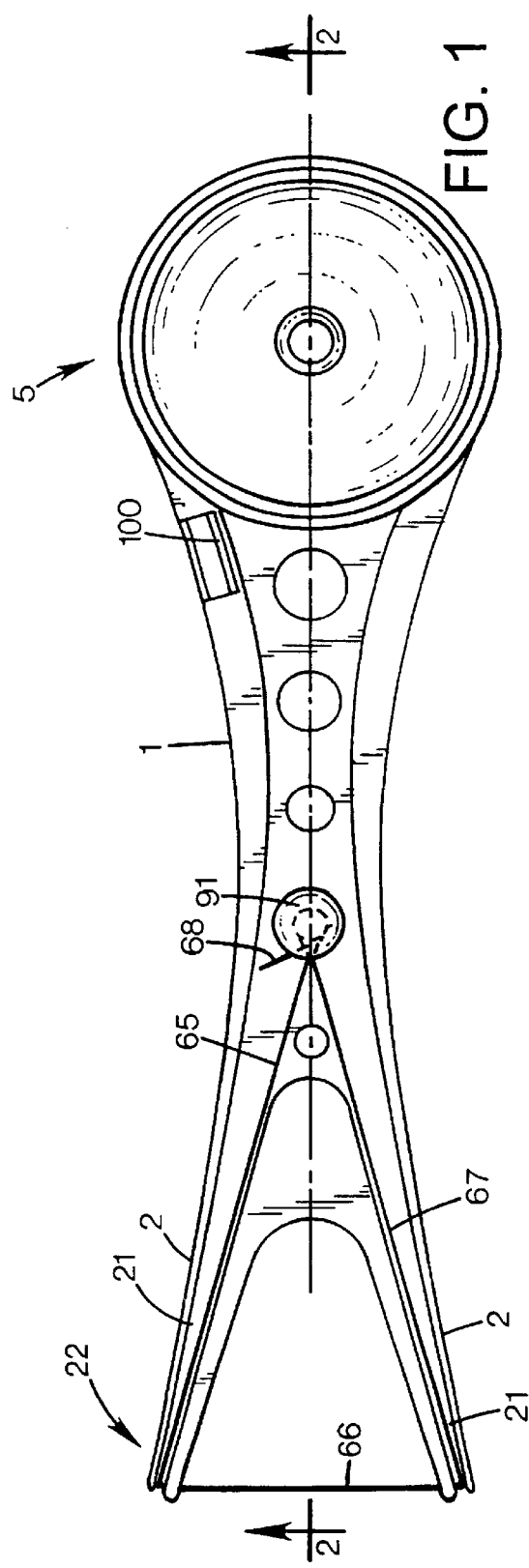
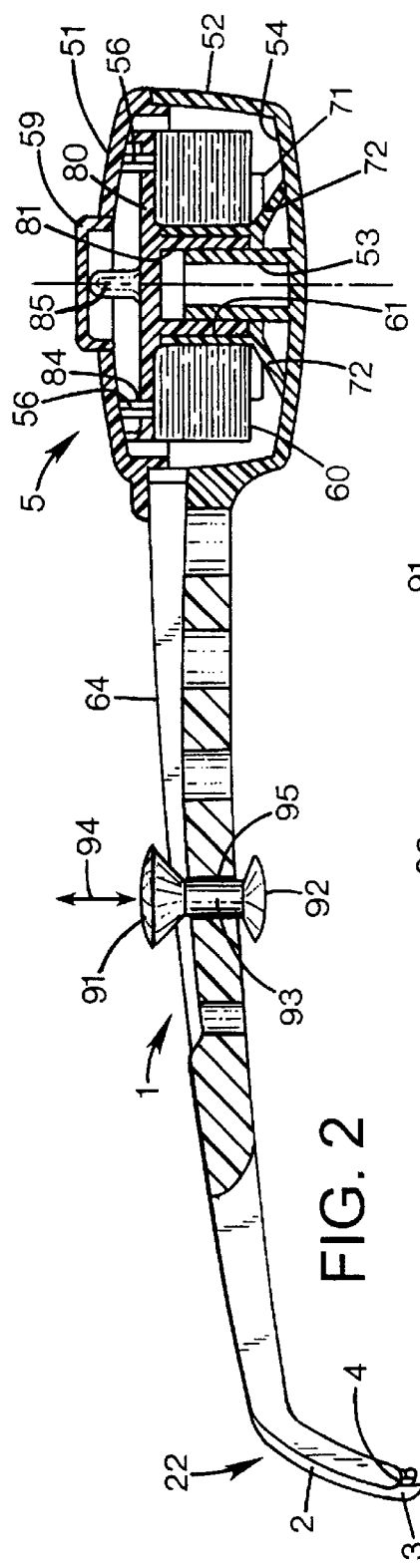
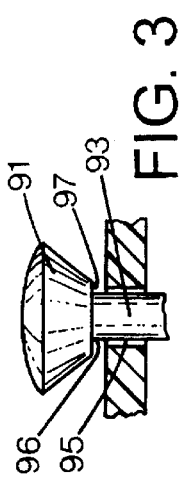

DENTAL FLOSS HOLDER

The invention relates to a dental floss holder that includes a member that carries a dental floss supply, and has a fork formation at one end so that the dental floss holder has a track to permit a piece of the dental floss to be tightened between the free ends of the fork fingers.

Prior known dental floss holders have, in practice, the drawback that they do not permit an easy and stable attachment of the ends of the dental floss segment to be extended between the outer ends of the fork fingers.

One object of the invention is therefore to provide a dental floss holder of the mentioned type that provides a simple and stable attachment of the ends of the dental floss segment that is tightened and extending across the fork fingers and that also provides an easy removal of the used dental floss segment.

Another object is to provide a dental floss holder that has a supply that easily provides a new dental floss segment.

The object of the invention is completely or partly achieved with the dental floss holder according to the appended claim 1.

Embodiments of the dental floss holder of the present invention are described in the dependent patent claims.

According to a fundamental distinctive feature of the invention the dental floss supply is formed by a roll or a spool of dental floss so that the roll is mounted with its axle across the longitudinal axis of the holder body so that the dental floss from the roll to the fork extends substantially radially to the roll. Further, a catch member is available to prevent the roll from rotating. In this way, the end portion of the dental floss segment that is to be used is attached simply because it cannot be pulled out from the roll due to its orientation relative to the load direction of the end of the dental floss.

The dental floss thus extends from the roll along the body to one of the fork finger ends and from there to the other fork finger end and then back along this fork finger to the attachment mechanism on the body. The fork fingers can be bent to make the teeth cleaning easier with the dental floss segment that extends between the fork finger ends.

In the preferred embodiment there are manually operable release members provided to temporarily release the rotational lock of the dental floss roll so that there is a bearing that permits rotation of the roll.

An example of the embodiment of the dental floss holder of the invention is shown in the attached drawings and is described in more detail below.

FIG. 1 shows a plan view of the dental floss holder of the invention.

FIG. 2 shows a section view along line II—II of FIG. 1.

FIG. 3 shows an enlarged view of a detail of the attachment mechanism of the free end of the dental floss.

FIG. 1 shows an elongate dental floss holder member that at one end has a dental floss supply 5 and at the other end has a pair of bent fork fingers 2. In the middle of the length of the member 1 there is an attachment mechanism for a dental floss end 68. The mechanism includes an opening 95 extending through the member 1. A shaft 93 extends through the opening and has heads 91, 92 at each end. The shaft 93 is slightly longer than the opening 95 so that the shaft 93 is lengthwise shiftable as indicated by the double arrow 94.

One can see that the member 1 has, on its upper side and along the fingers 2, a track 21 all the way to the finger points 3 where the track 21 extends into a guidance angle 4. In the supply 5, there is a dental floss roll 60 from which the dental floss extends out through an opening in the supply housing.

The floss is shown to have a first segment 64 from the roll 60 that extends partially around the shaft 93 wherefrom a subsequent floss segment 65 extends along the track 21 on one side of the fork finger 2 to the point 3 and further through the cavity 4 where the subsequent floss segment 66 extends to the next fork finger point 3 and through its cavity 4 wherefrom the next floss segment 67 extends in the track 21 on the fork finger 2 back to the shaft 93, and for example around the shaft and ends at the floss end 68.

With reference to FIG. 3, one can see a right angle 97 between the shaft 93 and the member 91. The free end 68 of the floss is received in the right angle 97. Further, one can see that the opening 95 has a chamfered end part 96. Further, the gap 95 between the opening 95 and the shaft 93 is adapted to the thickness of the dental floss. The dental floss end 68 can now be easily attached by pushing down the knob 91 in FIG. 2 so that the floss is captured in the gap 95. The end of the floss can be easily released by pushing the knob 92 in an upward direction (FIG. 2).

The member 1 can have a floss cutting tool 100.

The supply 5 has the shape of a bowl 52 with a bottom 54 and a lid 51. The center part of the lid 51 includes a manually resilient deformable membrane 59.

The bottom 54 has a central shaft bearing 53. This holds a socket 81 for rotation. An upper end of the socket 81 supports an end plate 80.

An inside of the lid 51 has a number of axially directed locking members 56. The end plate 80 has suitable axial channels 84 that receive the ends of the members 56. The socket 81 receives, with high friction, the reeling in casing 61 of the dental floss spool 60.

From the bottom 54, the socket 81 is supported by a support plate 71 that supports an end of the socket 81 (and also the roll 60). The plate 71 in turn is supported from the bottom 52 via spring fingers 72.

The spring fingers 72 holds the plate 80 in engagement with the members 56.

The plate 80 includes a pin 85 and extends to an inside of the membrane 59. A user can now easily with one finger apply a pressure from the outside against the membrane 59 so that the pin 85 and the plate 80 axially shift away from the engagement with the catch members 56 so that the plate 80 and thus the socket 81 and the floss roll 60 can freely rotate so that the floss 64 can be pulled out from the supply 5 to a desired length. As soon as the load on the membrane is removed, the floss roll 60 will, after some further turning by the continued pulling of the floss, to be rotationally locked.

In FIG. 2 one can see that the separate and generally parallel fingers 2 have a bent portion 22 at about half its length which makes it easier to work with the floss segment 66 between teeth.

What is claimed is:

1. A dental floss holder comprising:
    an elongate handle member having two fork fingers at one end thereof;
    a floss supply mounted to the handle member, the floss supply having a dental floss disposed therein and adapted to pull out the dental floss therefrom;
    the fork fingers having points including guidance members for permitting a floss segment of the dental floss to extend between the points;
    an attachment member attached to the handle member for attaching a floss end of the dental floss to the handle member;
    a floss roll disposed in the floss supply, the floss roll having a rolling axle mounted to the handle member and extending perpendicularly to the handle member;

locking members in operative engagement with the floss roll to lock the floss roll from rotation, the floss roll being coaxially attached to a roll holder being rotatably attached to the handle member about a bearing axle thereof;

the roll holder being axially spring biased against an end position to lock and prevent the roll holder from rotation, the roll holder having an end plate with openings defined therein for receiving the locking members to prevent the floss roll from rotation when the locking members extend through the openings of the end plate; and a membrane member in operative engagement with the end plate of the roll holder, the membrane member being manually operable for shifting the end plate of the roll holder away from engagement with the locking members to permit the end plate and the roll holder to rotate to enable the pulling out of the dental floss from the floss supply.

2. The dental floss holder according to claim 1 wherein the membrane member is provided to release the looking members from locking the floss roll, and the floss roll has bearings for rotation inside the floss supply.

3. The dental floss holder according to claim 1 wherein the attachment member has an opening defined therein that extends through the handle member, a shaft extends through the opening and is axially shiftable along the opening of the attachment member, the shaft has a head portion at one end of the shaft so that the dental floss extends about the shaft between the head portion and the handle member.

4. The dental floss holder according to claim 1 wherein the fork fingers have a track defined therein for guiding the dental floss to and from the points.

* * * * *